United States Patent [19]

Cornellier et al.

[11] Patent Number: 4,683,891

[45] Date of Patent: Aug. 4, 1987

[54] BIOMONITORING STRESS MANAGEMENT METHOD AND DEVICE

[76] Inventors: Vincent Cornellier, 1970 Connolly, Troy, Mich. 48084; Thomas K. Ziegler, 2058 Franklin, Berkley, Mich. 48072

[21] Appl. No.: 700,376

[22] Filed: Feb. 11, 1985

Related U.S. Application Data

[63] Continuation-in-part of Ser. No. 371,917, Apr. 26, 1982, abandoned.

[51] Int. Cl.$^4$ .............................................. A61B 5/00
[52] U.S. Cl. ................................... 128/630; 128/668; 128/672; 128/687; 128/716; 128/734; 128/905; 434/236
[58] Field of Search .............. 128/630, 731, 732, 733, 128/734, 670, 671, 905, 672, 736, 716; 273/1 GC, 1 GE; 272/DIG. 6; 434/238, 232, 258, 236

[56] References Cited

U.S. PATENT DOCUMENTS

| | | | |
|---|---|---|---|
| 2,944,542 | 7/1960 | Barnett et al. | 128/653 |
| 3,395,698 | 8/1968 | Morehouse | 272/DIG. 6 |
| 3,579,865 | 5/1971 | Walker | 434/258 |
| 3,691,652 | 9/1972 | Clynes | 434/236 |
| 4,184,485 | 1/1980 | Agoston | 128/670 |
| 4,354,505 | 10/1982 | Shiga | 128/905 |
| 4,408,613 | 10/1983 | Relyea | 272/DIG. 6 |
| 4,464,121 | 8/1984 | Perelli | 434/236 |

OTHER PUBLICATIONS

Thought Technology Ltd, product catalog, Biofeedback for Optimum Stress Management.

*Primary Examiner*—Kyle L. Howell
*Assistant Examiner*—John C. Hanley
*Attorney, Agent, or Firm*—Cullen, Sloman, Cantor, Grauer, Scott & Rutherford

[57] ABSTRACT

A method of managing and controlling stress in a person engaged in a goal oriented, cognitive task involves simultaneous measurement of a physical parameter of the person which varies in accordance with the level of the person's stress and the productivity of the person performing the task. A programmed computer calculates the stress point for the person beyond which productivity decreases and provides a visual display of the physical parameters and stress point on a cathode ray tube.

26 Claims, 7 Drawing Figures

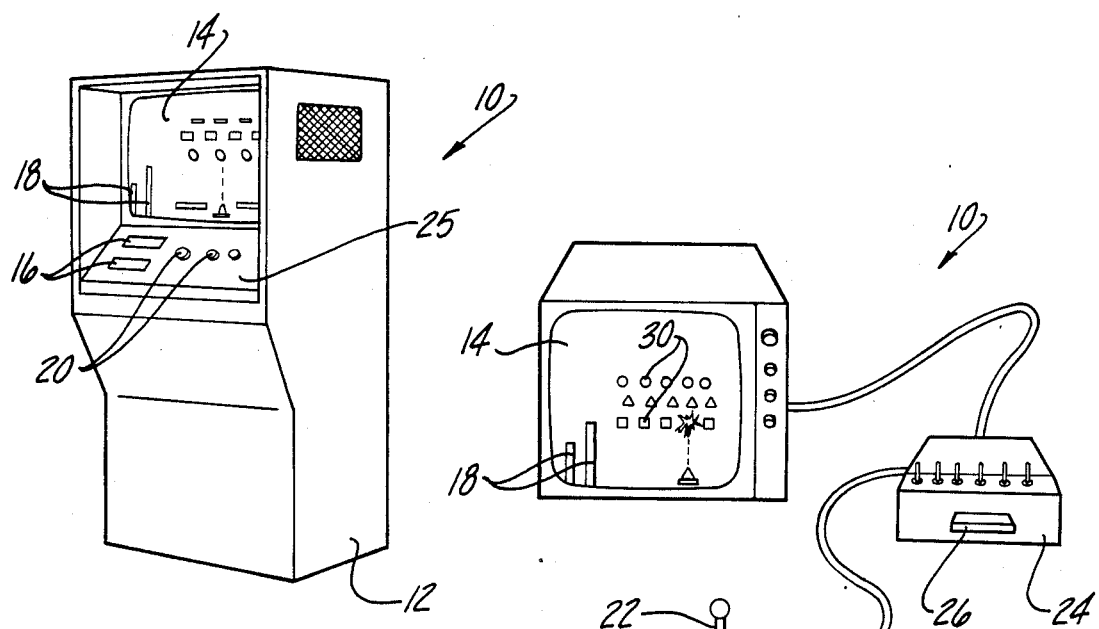
Fig-1
Fig-2
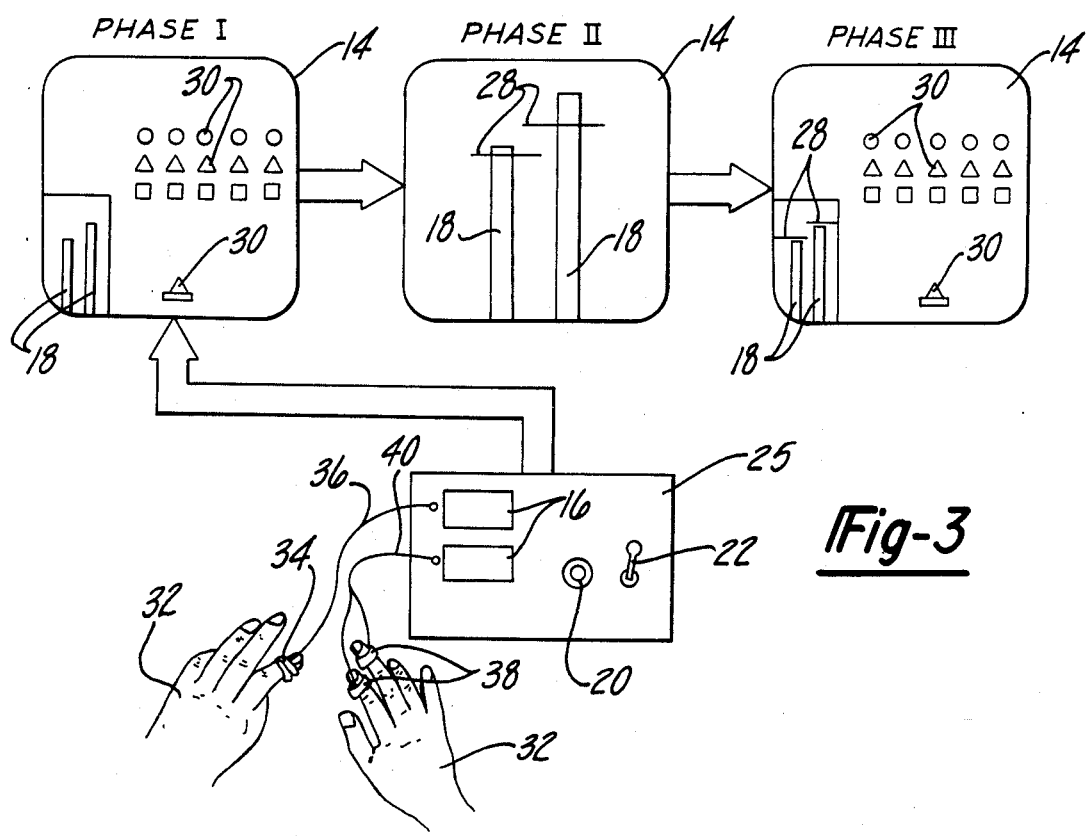
Fig-3

BIOMONITORING STRESS MANAGEMENT METHOD AND DEVICE

RELATED APPLICATIONS

This is a continuation-in-part application of U.S. patent application Ser. No. 371,917 filed Apr. 26, 1982, now abandoned.

TECHNICAL FIELD

The present invention broadly relates to biomonitoring of human beings, and deals more particularly with a system for improving the performance of tasks by humans through management or reduction of stress.

BACKGROUND ART

Many of the principles of the theory of human learning are based upon the fundamental relationship between the anxiety (sometimes referred to as "arousal") level of an individual and his or her test performance. It it relatively well established that as anxiety increases, test performance also increases in a linear manner until a "stress point" is reached following which there is a precipitous drop in performance. Anxiety manifests itself both psychologically and physically and the resulting stress induced by such anxiety may be referred to as "psychophysiological stress".

A number of recent studies have been made involving measurement of anxiety as a function of elapsed time per test question, and self-report (questionnaires) data regarding anxiety level. These subjective measurements are then compared to the ratio of right and/or wrong answers, or alternatively, are compared to a measure of productivity on the test itself. As a result of the above discussed research, it has been established that an individual's productivity, in terms of performing goal oriented tasks, increases until a so-called stress point is reached. Beyond the stress point, productivity is negatively affected by anxiety. In the past, primarily behavioral techniques have been applied to reduce anxiety and thereby increase productivity.

One of the problems associated with prior attempts at correlating anxiety with the test performance involves the fact that these parameters were not measured simultaneously. For example, a subject was first trained to reduce anxiety following which the subject was tested to determine the effects of any behavior modifications resulting from the training. This approach to the problem is undesirable, however, because the subject is unaware during the test of his stress point for the particular task he is performing as well as his level of stress relative to that point.

Physiological monitoring, more popularly known as biofeedback, of stress related disorders has been used with increasing frequency in recent years. Biofeedback training has been applied to the treatment of stress related disorders such as tension headaches, migraine headaches, colitis and other disorders of the autonomic and peripheral nervous system. Such training has also been resorted to assist test anxious individuals in learning a relaxation response which can be applied when the subject is undergoing testing.

U.S. Pat. No. 4,343,315 to John B. O'Leary discloses a method and apparatus for measuring the physical condition of a person. The apparatus comprises a portable heart monitor attached to a person and a plurality of circular foot paths positioned for sequential use by the person in order of increasing size. Marks are provided on the paths which indicate a fractional part of the circle to be covered in a measured number of seconds. A timer announces a tone at the end of the measured number of seconds to allow the person to pace himself in coverng the fractional parts in the required time interval. The heart monitor provides an alarm in the event that the person's heartbeat exceeds a safe level. The person is instructed by an observer to move to successively larger circles which require the person to increase his pace in order to traverse the fractional parts in the same time interval, thus causing the person's heartbeat to increase.

The objective of the O'Leary method described above is to monitor a physical parameter of the test subject, i.e., heartbeat. The test subject may or may not experience anxiety as a result of the test, but in any event the parameter being monitored is a physical one (heartbeat) and the changes in this physical parameter result from the test subject's physical activity rather than from psychological stress. More importantly, the task (traversing successively larger circles) is not changed in accordance with the monitored information; in other words, the task is altered without regard to the person's performance or the stress experienced by the person.

None of the known methods or apparatus used in the treatment of stress related disorders has successfully correlated an individual's performance of a goal oriented task with anxiety as measured by the subject's physiological response during performance of the task. It is therefore a primary object of the present invention to provide a device implemented method for controlling stress of an individual engaged in a goal oriented, cognitive task.

Another object of the invention is to provide a device implemented method on the type mentioned above which calculates the individual's stress point during performance of the task and provides the individual with an indication of such stress point. As a corollary to the foregoing object, it is a further object of the invention to provide the subject with an indication of the level of stress he or she is experiencing relative to his or her stress point.

Still another object of the invention is to provide a device implemented method as described above which progressively increases the difficultly of the task in accordance with the individual's stress tolerance thereby to increase his stress point and productivity.

Another object of the invention is to provide a method for managing the stress of a person engaged in a goal-oriented, cognitive task in which the person's performance is combined with the person's physiological response to form feedback data that is used to alter the task in a manner which increases the person's stress tolerance.

These, and further objects of the invention will be made clear or will become apparent during the course of a description of the invention provided hereinbelow.

DISCLOSURE OF THE INVENTION

According to the present invention, a method of controlling psychophysiological stress in a person engaged in a goal-oriented, cognitive task comprises the steps of measuring a physical parameter of the person which varies in accordance with the level of stress experienced by the person; measuring the performance of the person in accomplishing the tasks; calculating the anxiety induced stress level for the person beyond which the level of performance descreases; providing the person with an indication of such stress level; and then altering the difficulty of the task when such stress level is reached. In order to initially establish the stress level, the difficulty of the task is increased until a reduction in productivity is detected. The method may be practiced using an interactive video apparatus which includes a cathode ray tube for displaying a game or other characters generated by a programmed computer which provides a cognitive task to be performed by the person. The computer receives physiological parameters from the person as well as control signals produced by manually operable data input means controlled by the person. The computer is responsive to the physiological parameters and manual data input for calculating the person's stress level and providing a display of the physiological parameters and stress level on the CRT. The computer also stores data corresponding to the calculated stress level and includes a program which alters the game or other task in a manner which teaches the person to increase his or her stress level.

BRIEF DESCRIPTION OF THE DRAWINGS

In the drawings, which form an integral part of the specification and are to be read in conjunction therewith, and wherein like reference numerals are employed to designate identical components in the various views:

FIG. 1 is a perspective view of one form of the device for practicing the method of the present invention;

FIG. 2 is a perspective view of another form of the device for practicing the method of the present invention;

FIG. 3 is a diagrammatic view of a device similar to that shown in FIGS. 1 and 2, showing the connection between an operator and the device, and also depicting a series of views on the screen corresponding to successive phases of the method for reducing stress;

BEST MODE FOR CARRYING OUT THE INVENTION

Figure 4:
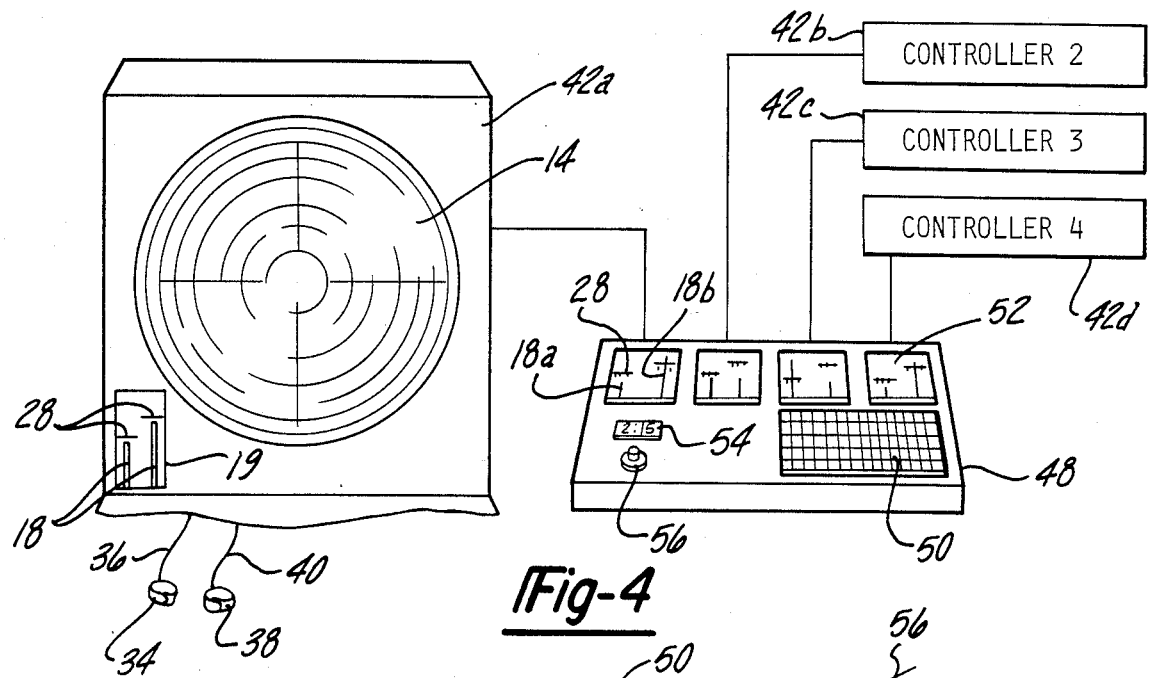
FIG. 4 is an alternate form of the device for practicing the method of the present invention.

Referring first to FIGS. 1-3, the present invention is broadly concerned with a biomonitoring stress management method and device useful for reducing stress in human beings or, conversely, for increasing a person's performance in connection with goal oriented, cognitive tasks. The stress with which the present invention is concerned is of the type induced by the psychological anxiety when a person is engaged in a goal oriented, cognitive task. As discussed above, it is well-known in the art that psychological anxiety manifests itself both psychologically and physically. Psychological manifestations may include changes in cognition, perception, reasoning, etc., while physical manifestations of psychological anxiety may consist, for example, of increased muscle tension or weariness, a change in galvanic skin reaponse, changes in EKG patterns, pulse rate, etc. Thus, the type of stress being measured and managed in the present context is of a "psychophysiological" type having both physical and mental components, which is brought about by mental anxiety.

As shown in FIG. 1, the device, broadly indicated by the numeral 10, may consist of a console 12 provided with a conventional CRT (cathode ray tube) 14 and a control portion 25. Control portion 25 is provided with one or more, manually operable control handles or buttons 20 and a pair of conventional electronic displays 16 for reading out digital data.

As shown in FIG. 2, the device 10 may alternatively consist of a CRT 14 in the form of a conventional television monitor electrically interconnected with a control module 24 which is adapted to receive a cartridge 26 of magnetic tape upon which programmed instructions are stored for generating various types of video games or other characters on the screen 14. The control portion 25 may include a so-called manually operated "joy stick" 22 coupled with the control module 24 in order to allow an operator to manually control data or events occurring on the CRT 14.

The control portion 25 may also be of a form as shown in FIG. 3 provided with a control button 20 and control stick 22 for manipulating events on CRT 14, as well as a pair of digital read out displays 16 whose purpose will be discussed below.

Each of the devices 10 shown in FIGS. 1-3 is provided with means for sensing a physical parameter of an operator in order to sense the level of stress being experienced by the operator while manipulating characters or events on the CRT 14 with the control portion 25. As shown in FIG. 3, the above mentioned sensing means may comprise a thermistor type electrode 34 coupled to the console 25 by line 36 and mounted on a finger of the operator's hand 32 by a so called velcro strip or the like. Additional electrodes 38 coupled to the console 25 by line 40 and fastened to the operator's hand 32 provide electrical signals corresponding to the operator's temperature. In the case of the device shown in FIGS. 1 and 2, electrodes 34 and 38 may be incorporated integral with the control knobs 20 and stick 22 if desired. The term "physical parameter" as used herein is inteded to mean virtually any quantifiable physiological function of the human body which varies in relation to the degree of psychological stress experienced by the individual. Such parameters include galvanic skin response, temperature, respiration, blood pressure, pulse rate and various type of bioelectrical responses.

As will be discussed later in more detail, the device 10 includes a computer programmed to provide a moving display of characters 30 on the CRT 14. This display may consist of a conventional game wherein at least some of the characters may be controlled by the operator through the control portion 25. The operator's physiological response is measured by electrodes 34 and 38 while the game is being played. As shown in FIG. 3, the device 10 may be programmed to function in three distinct phases. Initially, during Phase I; the operator's stress point is established by continuously measuring his physiological parameters as he views the CRT 14 and manipulates characters 30 using the control portion 25. The operator's physiological parameters are displayed at 18 in the lower left hand corner of the CRT 14. A programmed computer forming a part of the device 10 produces a preprogrammed display such as a game, on the CRT 14 and continuously measures the productivity or success of the operator in playing the game or othewise responding to the display. The computer also successively increases the difficulty of the game until the operator's success or productivity commences to decrease.

During Phase I, when the operator reaches his stress point, i.e., when his measured game performance begins to decrease, the computer records such as stress point, interrupts the game, disables manual control by the operator and displays the bar graphs 18 in a full screen fashion, as shown in the view designated by the legend "Phase II" in FIG. 3. The stress point is also displayed as a horizontal mark 28 superimposed on the bar graphs 18. Since the CRT 14 no longer displays the characters 30 and the control portion 25 is disabled, the operator is in a position to lower his anxiety level through conventional biofeedback techniques, using the bar graphs 18 on CRT 14 and/or the digital readout 16 which provide a digitized indication of the parameters shown on bar graphs 18. Phase II continues until the operator is able to relax sufficiently that his physiological parameters fall below the stress point 28 established during Phase I. When the operator's anxiety level falls below stress point 28, Phase III of the program is commenced in which the game displayed on CRT 14 is resumed and operator control is restored; the bar graph and stress point display revert to the lower left hand corner of the CRT 14. At this point, the operator may resume control of the game or other task involving the input of data and display thereof on CRT 14; the bar graph display 18 then provides continuous feedback of his stress level to aid the operator in maintaining his anxiety below the stress point 28. However, in the event that the operator's stress level exceeds stress point 28, the system operation reverts to Phase II as previously described until the operator is able to reduce his stress level below the previously established stress point 28.

It should be noted here that one or more manual controls such as the graduated slide dials 17 may be provided to allow the operator to manually set his or her stress point. In this manner, the computer control of the stress point setting can be effectively overridden and the operator can manually increase the stress point as desired.

If desired, the computer program may include a subroutine which constantly or periodically recalculates the stress point 28 as the productivity-to-stress level ratio is improved. In this manner, the operator can establish progressively higher stress points so as to maximize productivity with minimum attendant stress. As will be discussed later, in this mode of operation, data corresponding to the stress point is stored in a memory and this data is successively updated each time the stress point 28 is recalculated.

It is contemplated that the method of the present invention may be carried out in a number of alternate ways in contrast to the phased mode of operation described above. The significant feature of the method which is inherent in the mode of operation previously described consists of feeding back to the operator information concerning his or her stress point relative to performance in terms of the task being performed. This is accomplished in the scheme described above by interrupting the display during Phase II and then resuming the task oriented display in Phase III when the operator's stress level drops below a threshold value. However, the method can be implemented in other ways; for example, such feedback information could be provided to the operator by simply altering the nature of the task being performed. Thus, with reference to FIG. 3, rather than interrupting the display of the characters 30 when the stress point is reached, the nature of the characters or the difficulty of the "game" could be automatically altered by the computer's software to alert the operator that the stress point had been exceeded. By reducing the difficulty of the task (via software control), the operator's stress would then be reduced below the threshold value, and after a selected period of time, a higher level of difficulty could be resumed. In summary, the method described immediately above can be implemented by the following steps: measuring a physical parameter of a person while the person is performing a goal oriented, cognitive task, wherein the measured parameter is one which varies in accordance with the level of psychophysiological stress experienced by the person; measuring the performance of the person in accomplishing the task; determining a first level of stress for the person beyond which level the performance of the person in accomplishing the task does not substantially increase; storing data corresponding to the first determined stress level; providing the person with an indication of the first stress level while the person is performing the task, thereby allowing the person to reduce the stress level through relaxation response or "biofeedback"; increasing the difficulty of the task; again measuring the physical parameter and the performance of the person in accomplishing the task, the difficulty of which has been increased; determined a second stress level which is higher than the first and beyond which the performance of the person does not substantially increase; storing data corresponding to the second determined stress level; providing the person with an indication of the second stress level while the person is performing the task, thus allowing the person to reduce the stress level through biofeedback.

The method and apparatus described above may also be employed in a system in which a number of operating stations are controlled by a central computer, and in this respect, reference is also now made to FIG. 4. One typical application of the multistation form of the present invention is an air traffic control system in which a plurality of controllers 42a, 42b, 42c and 42d, each attended by an operator, are controlled and monitored at a central operating station 48. Each of the controllers 42 is provided with a CRT 14 for displaying data, such as the location and altitude of aircraft, and data input means (not shown) such as a keyboard. Additionally, a data display 19 is provided similar to that previously described for displaying bar graphs 18 and stress points 28 associated with the operator at the corresponding controller 42. Again, sensing devices 24 and 28 are provided at each controller 42 for monitoring selected physical parameters of the operator, such as galvanic skin response and temperature.

The central station 48 is provided with a plurality of displays 52 respectively associated with each of the controllers 42 for providing a readout of data identical to the display 19 at the corresponding controller 42. A conventional keyboard 50 is provided for inputting data into a computer which forms part of the central station 48. A digital readout 54 is provided for displaying elapsed time and a switch 56 allows the operator to switch any of the controllers 42 which has been addressed by keyboard 50, between a standard operating state and a feedback state employing the method of the present invention.

In operation, the stress point 28 of the operator associated with each controller is established in a manner identical to that previously described. Thereafter, the operator's physical parameters as well as his stress point may be monitored at the central station 48. The program for calculating the stress points and productivity-to-stress ratio may be conveniently altered by way of the keyboard 50. Additionally, the keyboard 50 may be used to manually establish the stress points, and thereby override computer control of these parameters. Operation of switch 56 selectively disables the display 19. In this manner, the operator at the central station module 48 may enable display 19 at selected controllers 42 only when the associated operator's stress level exceeds stress point 28 as shown on the displays 52.

Figure 5:
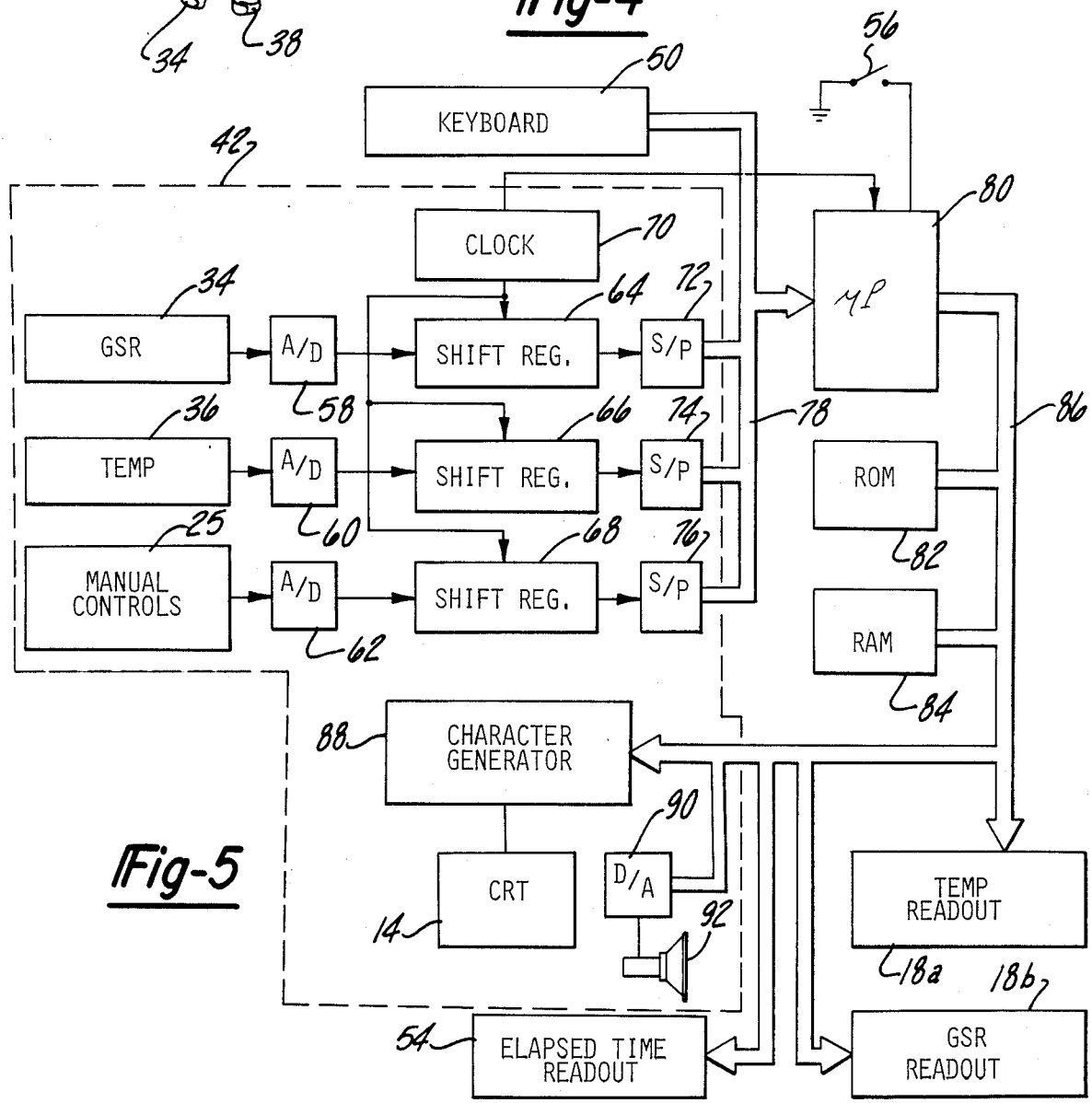
FIG. 5 is a combined block and schematic diagram of a circuit for use in the devices shown in FIGS. 1-4.

Attention is now directed to FIG. 5 wherein one suitable circuit for carrying out the system of FIG. 4 is depicted. Each of the controllers 42 is operably coupled to the data input terminals of a conventional microprocessor 80. Controller 42, as previously indicated, includes physiological sensing devices 34 and 36 as well as a set of manual controls 25 (such as a keyboard) for controlling data displayed on CRT 14. Data produced by devices 34 and 36 as well as manual controls 25 are delivered to corresponding A to D converters 58–60 which convert the analog information to digital data. The digital data is then delivered to corresponding shift registers 64–68 which essentially function to hold and accumulate data in serial form. The serial data is delivered from shift registers 64–68 to respectively associated serial-to-parallel converters 72 and 76 which convert the serial information to parallel form. The parallel data is output onto a data bus 78 which is coupled to the parallel data input ports of microprocessor 80. Keyboard 50 is likewise coupled to the data input ports of microprocessor 80 via data bus 78. Microprocessor 80 is a conventional device such as that manufactured by the Motorola Corporation and identified by the manufacturer's number 6800. Microprocessor 80 has data and control outputs coupled by a data bus 86 to a read only memory (ROM) 82 and a ram access memory (RAM) 84. RAM 84 is provided with a program for temporarily storing input variables received from microprocessor 80, including physiological parameters and calculated stress points, and for converting such variables to addresses which are used to address storage locations in ROM 82. ROM 82 is programmed to control the data displayed on CRT 14 in accordance with the method previously described. Those skilled in the art may readily devise suitable programs for ROM 82 in accordance with the method of the present invention and a detailed description of such program therefore have not been provided herein. However, flow charts for one suitable program are shown in FIGS. 6 and 7 for illustrative purposes.

Figure 6:
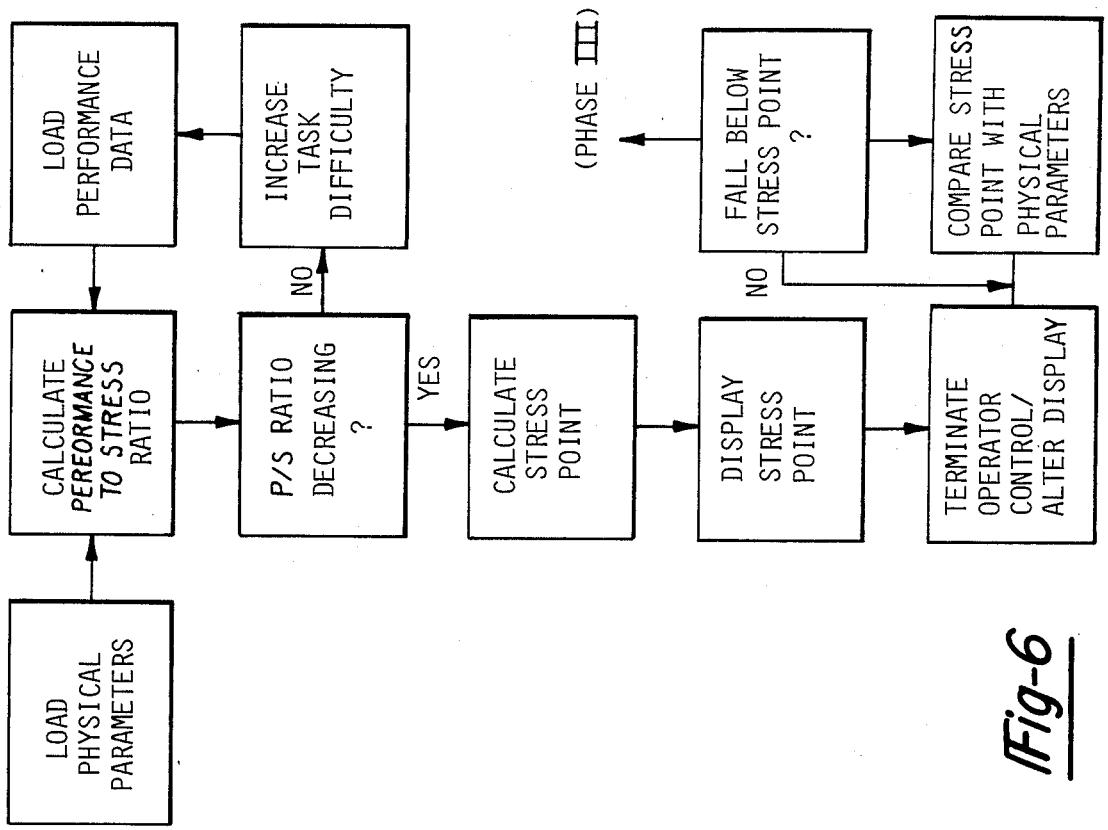

The program for operating the computer during Phases I and II is shown in FIG. 6. The first program step associated with Phase I involves loading the physical parameters (GSR, temperature, etc.) and performance data following which the performance-to-stress ratio is calculated. The program then determines whether the performance-to-stress ratio is decreasing. If such ratio is not decreasing, the program increases the difficulty of the task (e.g. increases the difficulty of the game or other character display to which the operator must respond), and the performance-to-stress ratio is recalculated. If the ratio commences decreasing, the stress point is calculated and displayed. At this point, the program terminates operator control and alters the display to a biofeedback presentation, as depicted by Phase II in FIG. 3. The program then commences continually comparing the operator's physical parameters with the calculated stress point until such parameters (which indicate stress level) fall below the stress point whereupon that portion of the program shown in FIG. 7, corresponding to Phase III, assumes control.

Figure 7:
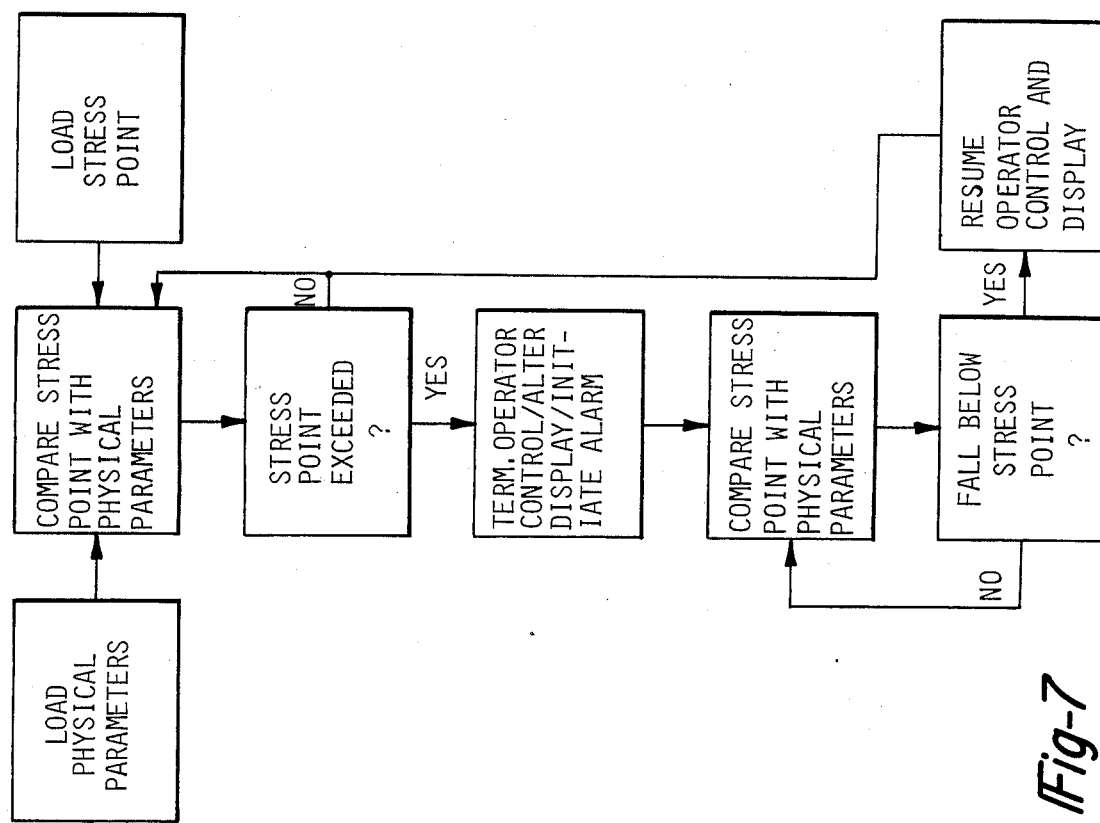
FIGS. 6 and 7 are flowcharts of a program for use in the computer forming a portion of the device shown in FIGS. 1-5.

As shown in FIG. 7, the physical parameters and stress point are loaded into memory and the stress point is then compared with the physical parameters. The comparison is continued until the stress point is exceeded at which time operator control is termined, the display is altered as previously described and an alarm may be initiated. At that point, the system has reverted from Phase III to Phase II. The operator's physical parameters continue to be compared to the stress point until they fall below such point at which time operator control is resumed and the display is reinstated as shown Phase III of FIG. 3.

Returning to FIG. 5, data is delivered via data bus 86 to a character generator 88. Character generator 88 is conventional in design and includes a memory addressed by the signals on data bus 86 which produces predefined video signals that are delivered to CRT 14 for display.

Data is also delivered on data bus 86 to a temperature readout 18a, GSR readout 18b, and elapsed time readout 54. Additionally, digital signals on data bus 86 are converted by a D to A converter 90 to drive a speaker 92 which forms an alarm to provide an audible indication when the stress point is reached.

INDUSTRIAL APPLICABILITY

The method and device previously described are well adapted for use in various applications in which an individual is engaged in goal oriented tasks which tend to induce stress.

From the foregoing, it is apparent that the device and method of the present invention not only provides for the reliable accomplishment of the objects of the invention but do so in a particularly effective and efficient manner. It is recognized, of course, that those skilled in the art may make various modifications or additions to the preferred embodiment chosen to illustrate the invention without departing from the spirit and scope of the present contribution to the art. Accordingly, it is to be understood that the protection sought and to be afforded hereby should be deemed to extend to the subject matter claimed and all equivalents thereof fairly within the scope of the invention.

I claim:

1. A method of increasing a person's ability to perform under anxiety induced, psychophysiological stress, comprising the steps of:
    (A) providing a computer controlled device including an interactive communication link between said device and said person;
    (B) programming said computer for controlling said device to create a task of progressively increasing difficulty to be accomplished by said person whih creates anxiety in said person;
    (C) determining the level of psychophysiological stress of said person induced by said anxiety beyond which the performance of said person in accomplishing said tasks decreases;
    (D) providing said person with an indication of the level of psychophysiological stress determined in step (C);
    (E) allowing said person's stress level to fall below the level indicated in step (D), then changing said task in a manner to increase the stress level experienced by said person in accomplishing said task.

2. The method of claim 1 wherein step (E) is performed by programming said computer to automatically increase the difficulty of said task in response to the person's stress level falling below the level determined in step (c).

3. The method of claim 1, wherein step (C) is performed by:
monitoring the performance of said person in accomplishing said task,
monitoring the physiological parameter of said person which varies in accordance with the magnitude of psychophysiological stress experienced by said person in accomplishing said task, and
determining said level using the monitored performance and the monitored physiological parameter.

4. A method of managing anxiety induced stress level in a person engaged in a goal oriented, anxiety producing task of progressively increasing difficulty, beyond which stress level the person's performance in achieving said task decreases, comprising the steps of:
(A) monitoring at least one physical parameter of said person which varies in accordance with the level of anxiety induced stress experience by said person;
(B) monitoring the performance of said person in accomplishing said task;
(C) determining a point in said task when the difficulty of said task causes the performance of said person to decrease while simultaneously determining the stress level of said person at said point from said physical parameter;
(D) altering the difficulty of said task when said point of step (C) is reached; and
(E) repeating steps (A) through (D).

5. The method of claim 4, wherein step (A) is performed by sensing the electrical resistance of the skin of said person.

6. The method of claim 4, wherein step (A) is performed by sensing the pulse rate of said person.

7. The method of claim 4, wherein step (A) is performed by sensing the blood pressure of said person.

8. The method of claim 4, wherein step (A) is performed by sensing the respiration of said person.

9. The method of claim 4, wherein step (C) is performed by determining the ratio of said monitored physical parameter to said monitored performance.

10. The method of claim 4, including the step of providing to said person an indication of the magnitude of the parameter monitored in step (A).

11. The method of claim 4, wherein steps (A) and (B) are performed substantially continuously and step (C) is repeated periodically.

12. The method of claim 4, further comprising the step of:
(F) providing to said person an indication of said stress level when said point is reached.

13. The method of claim 12, wherein step (F) is performed by generating a visual display indicative of the determined stress level.

14. The method of claim 12, wherein step (F) is performed by altering said visual display when the stress level determined in step (C) exceeds a previously determined level thereof.

15. A method of managing anxiety induced stress in a person, comprising the steps of:
(A) causing the person to undergo an anxiety producing, cognitive task;
(B) monitoring a physical parameter of said person which varies in accordance with the magnitude of anxiety induced stress experienced by said person during performance of said task;
(C) monitoring the ability of said person to perform said task;
(D) increasing the difficulty of said task;
(E) determining the magnitude of stress from the parameter monitored in step (B) when the difficulty of said task reaches a level thereof beyond which the ability measured in step (C) decreases;
(F) providing said person with an indication of the magnitude of stress determined in step (E);
(G) repeating steps (A) through (F) when the level of stress falls below the level indicated in step (F).

16. The method of claim 15, wherein step (B) is performed by sensing electrical signals obtained from the body of said person.

17. The method of claim 15, wherein step (A) is performed by:
providing a visual display,
providing a manually operable device for altering said visual display, and
manually operating said device.

18. The method of claim 17, wherein the step of providing a visual display is performed by generating video signals using a digital computer, and converting said video signals into visual indicia using a cathode ray tube, and step (D) is performed by altering said video signals in accordance with the magnitude of stress determined in step (E).

19. The method of claim 15, wherein:
step (A) is performed by providing a visual display of characters and means operable by said person for altering the display of said characters, and
step (F) further including the steps of terminating said visual display of characters when said magnitude determined in step (E); and is reached and providing a visual display of said physical parameter monitored in step (B).

20. The method of claim 19, including the step of resuming the visual display of said characters following termination thereof after the magnitude of monitored stress falls below said level determined in step (E).

21. A method of increasing a person's ability to perform under anxiety induced, psychophysiological stress, comprising the steps of:
(A) causing said person to undergo an anxiety producing task of progressively increasing difficulty;
(B) monitoring a physical parameter of said person which varies in accordance with the magnitude of psychophysiological stress experienced by said person as a result of performing said task;
(C) monitoring the performance of said person in accomplishing said task;
(D) determining the level of stress beyond which said monitored performance decreases, using the monitored physical parameter and the monitored performance;
(E) providing said person with an indication of the level of said stress determined in step (D); and
(F) allowing said person to reduce said level of stress by biofeedback;
(G) after step (F), changing said task in a manner which increases the stress of said person in accomplishing said task.

22. The method of claim 21, wherein step (A) is performed by:

programming a computer with a series of tasks to be performed by said person, displaying indicia on a display which represent said tasks, providing an interactive link between said person and said computer for allowing said computer to respond to the psychophysiological stress experienced by said person in performing said tasks.

23. The method of claim 22, wherein step (A) is performed by programming said computer to automatically change said tasks in a manner to increase the anxiety of said person in accomplishing said tasks.

24. For use with a person engaged in a goal oriented, cognitive task which results in anxiety induced, psychophysiological stress in said person, a method of increasing the person's ability to perform under said stress, comprising the steps of:

(A) monitoring a physical parameter of said person while said person is performing said task, said parameter varying in accordance with the level of said stress;

(B) monitoring the performance of said person in accomplishing said task;

(C) determining a first level of said stress for said person from said parameter beyond which level the performance of said person does not substantially increase;

(D) storing data corresponding to said first stress level determined in step (C);

(E) providing said person with an indication of said first stress level determined in step (C) while said person is performing said task, whereby to allow said person to reduce said stress level through biofeedback;

(F) increasing the difficulty of said task after the person's stress level is reduced below said first stress level based on the data stored in step (D);

(G) repeating step (A);

(H) monitoring the performance of said person in accomplishing the tasks after step (F) is performed;

(I) determining a second level of stress greater than said first level beyond which the performance of said person does not substantially increase;

(J) storing data corresponding to said second stress level determined in step (I);

(K) providing said person with an indication of said second stress level determined in step (I) while said person is performing said task, whereby to allow said person to reduce said stress level through biofeedback.

25. The method of claim 24, wherein steps (D) and (J) are performed by writing said data into a memory, and step (F) is performed by reading said data from said memory using a computer.

26. The method of claim 24, including the step of, after completing step (K), increasing the difficulty of said task a predetermined amount.

* * * * *